(12) United States Patent
Takenaka

(10) Patent No.: US 7,727,767 B2
(45) Date of Patent: Jun. 1, 2010

(54) METHOD FOR QUANTITATIVE ANALYSIS OF METAL ELEMENT CONTAINED IN RESIN MATERIAL

(75) Inventor: Miyuki Takenaka, Yokohama (JP)

(73) Assignee: Kaushiki Kaisha Toshiba, Tokyo (JP)

( * ) Notice: Subject to any disclaimer, the term of this patent is extended or adjusted under 35 U.S.C. 154(b) by 896 days.

(21) Appl. No.: 11/517,407

(22) Filed: Sep. 8, 2006

(65) Prior Publication Data
US 2007/0026526 A1 Feb. 1, 2007

Related U.S. Application Data

(63) Continuation of application No. PCT/JP2006/306058, filed on Mar. 20, 2006.

(30) Foreign Application Priority Data

Mar. 31, 2005 (JP) .............................. 2005-101744

(51) Int. Cl.
G01N 33/20 (2006.01)
G01N 1/44 (2006.01)
G01N 21/73 (2006.01)
G01N 21/74 (2006.01)
G01N 33/44 (2006.01)

(52) U.S. Cl. .............................. 436/81; 436/73; 436/80; 436/82; 436/83; 436/84; 436/85; 436/171; 436/172; 436/173; 436/175; 436/181

(58) Field of Classification Search ................... 436/73, 436/80–85, 155, 171–173, 175, 181
See application file for complete search history.

(56) References Cited

U.S. PATENT DOCUMENTS

| | | | | |
|---|---|---|---|---|
| 3,854,979 | A | * | 12/1974 | Rossi .......................... 427/228 |
| 4,204,769 | A | * | 5/1980 | Lersmacher et al. ......... 356/244 |
| 4,816,338 | A | * | 3/1989 | Terasaki et al. .............. 428/408 |
| 5,252,267 | A | * | 10/1993 | Holcombe et al. .......... 264/432 |
| 5,259,856 | A | * | 11/1993 | Ohga et al. .................... 65/426 |
| 5,476,679 | A | * | 12/1995 | Lewis et al. ................. 427/122 |
| 5,476,795 | A | | 12/1995 | Osawa |
| 5,541,012 | A | * | 7/1996 | Ohwaki et al. .............. 428/690 |
| 5,911,824 | A | * | 6/1999 | Hammond et al. ............ 117/81 |
| 5,989,504 | A | * | 11/1999 | Wilson et al. ................ 423/23 |
| 6,143,412 | A | * | 11/2000 | Schueller et al. ............ 428/408 |
| 6,200,385 | B1 | * | 3/2001 | Swinehart .................... 117/220 |
| 7,064,927 | B2 | * | 6/2006 | Erickson et al. ............. 360/135 |
| 2003/0210496 | A1 | * | 11/2003 | Erickson et al. ............. 360/133 |
| 2005/0271556 | A1 | * | 12/2005 | Takenaka et al. ............ 422/102 |

FOREIGN PATENT DOCUMENTS

| | | |
|---|---|---|
| EP | 0 266 736 | 5/1988 |
| JP | 2002-261080 | 9/2002 |
| JP | 2005-61880 | 3/2005 |

OTHER PUBLICATIONS

Fetterolf, D. D. et al, Journal of Agriculture and Food Chemistry 1979, 27, 377-380.*
Kotz, L. et al, Talanta 1979, 26, 681-691.*
Wittmann, A. A. et al, Spectrochimica Acta Part B 1985, 40, 253-261.*
Wittmann, A. A. et al, Spectrochimica Acta Part B 1986, 41, 73-79.*
Hinners, T. A. et al, Analytical Chemistry 1987, 59, 2658-2662.*
Hill, S. J., Techniques and Instrumentation in Analytical Chemistry, 1992, 12, 231-255.*
Watmough, S. A. et al, Environmental Pollution 1996, 93, 93-102.*
Hoenig, M. et al, Spectrochimica Acta Part B 1996, 51, 1297-1307.*
Ernst, T. et al, Talanta 2000, 53, 347-357.*
Watmough, S. A. et al, The Science of the Total Environment 2002, 293, 85-96.*
Matusiewicz, H., Comprehensive Analytical Chemistry 2003, 41, 193-233.*
Botto, R. I., Comprehensive Analytical Chemistry 2003, 41, 683-721.*
Oikari, R. et al, Energy & Fuels 2003, 17, 87-94.*
Ritter, A. et al, Polymer Testing 2004, 23, 467-474.*
ISO 247:1990(E), Rubber—Determination of ash.
ISO 6101-2: 1997(E), Rubber—Determination of metal content by atomic absorption spectrometry—Part 2: Determination of lead content.

* cited by examiner

Primary Examiner—Arlen Soderquist
(74) Attorney, Agent, or Firm—Oblon, Spivak, McClelland, Maier & Neustadt, L.L.P.

(57) ABSTRACT

Disclosed is a method for the quantitative analysis of a metal element contained in a resin material, which permits quantitatively analyzing the harmful substance such as lead contained in a resin material, comprising decomposing the resin material within a container having at least the inner surface formed of a glassy carbon in the presence of an aqueous solution of an oxidizing acid, heating the organic residue of the decomposed resin material so as to convert the residue into an ash, and quantitatively measuring the metal element contained in the organic residue converted into the ash.

16 Claims, 1 Drawing Sheet

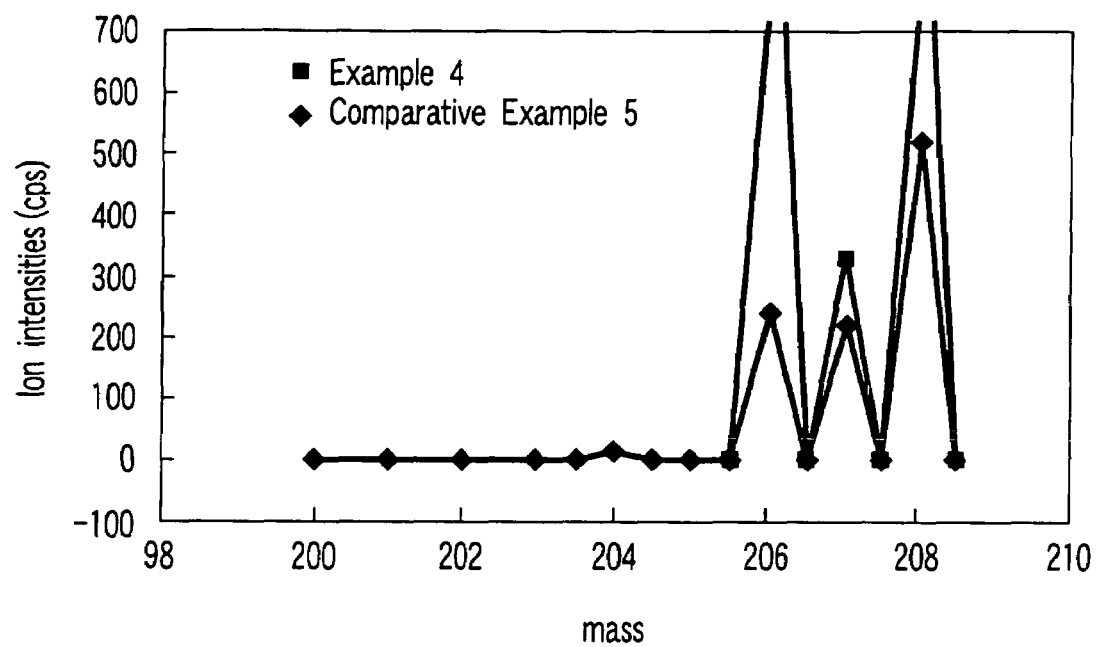
FIGURE

METHOD FOR QUANTITATIVE ANALYSIS OF METAL ELEMENT CONTAINED IN RESIN MATERIAL

CROSS REFERENCE TO RELATED APPLICATIONS

This is a Continuation Application of PCT Application No. PCT/JP2006/306058, filed Mar. 20, 2006, which was published under PCT Article 21(2) in English.

This application is based upon and claims the benefit of priority from prior Japanese Patent Application No. 2005-101744, filed Mar. 31, 2005, the entire contents of which are incorporated herein by reference.

BACKGROUND OF THE INVENTION

1. Field of the Invention

The present invention relates to a method for quantitative analysis of a metal element such as lead contained in a resin material.

2. Description of the Related Art

In recent years, legal regulations have been enforced over the world, with attention paid to the harmful properties of chemical substances. In the European Community, a legal regulation of Restriction of Hazardous Substances (RoHS) for restricting the use of specified substances was enforced in 2006 so as to regulate clearly that six kinds of harmful substances including lead (Pb) and cadmium (Cd) must not be contained in any electrical or electronic appliances. These legal obligations must be obeyed by not only manufacturers but also enterprises exporting electrical and electronic appliances to Europe. Under the circumstances, it is a serious responsibility that must be assumed by enterprises to grasp accurately the amount of the harmful substance contained in the electrical and electronic appliances and to certify that substances harmful to the environment are not contained in the electrical and electronic appliances.

Known methods of measuring Pb and Cd, which are harmful to the environment, include, for example, BSEN-1122 (2001) (Determination of Cadmium wet decomposition method), which is employed in Europe, and EPA method B (Acid digestion of sediments, sludge, and soils), which is an official regulation by the U.S. Environmental Protection Agency. In exporting electrical and electronic appliances to Europe and the U.S.A., it is necessary to measure individually the element specified in these official regulations.

The known methods for measuring the specified element includes, for example, a wet chemical analytical method in which an aqueous solution of an oxidizing acid such as nitric acid, hydrochloric acid, sulfuric acid, or hydrogen peroxide is added to a sample so as to decompose the inorganic material or the organic material forming the matrix of the sample. Also, the sample in the form of a solution is measured in general by inductively coupled plasma emission spectrometry or an atomic absorption method.

Also, an ashing method using a platinum crucible is proposed as a method for the quantitative analysis of lead in ISO6101-2 Rubber "Determination of metal content by atomic absorption spectrometry".

However, various problems arise in the conventional official regulations referred to above, as pointed out in the following:

(1) The methods specified in the official regulations necessitate troublesome analytical operations, and a long time is required for the decomposition so as to make the methods inefficient.

(2) Since sulfuric acid or hydrochloric acid is used in the wet acid decomposition method, lead is partly converted into lead sulfate or lead chloride. In other words, loss of lead is generated, with the result that the measured value is not reliable accurate.

(3) In the ashing method using a platinum crucible, Pb or Cd tends to be lost by the rapid heating so as to lower the accuracy of the analysis.

To be more specific, where the sample is formed of a resin material, particularly, polyvinyl chloride resin containing a large amount of chlorine (Cl), the chlorine contained in the resin is combined with the metal element that is to be measured so as to form a chloride, which tends to be evaporated easily.

Also, in the case of using a platinum crucible, a serious problem arises because platinum forms a solid solution with lead (Pb) that is to be measured. Specifically, Pb is adsorbed on the wall of the platinum crucible. Also, Pb is eluted as an impurity from the platinum crucible, or platinum itself is eluted so as to form a solid solution with Pb to be measured. As a result, an isotope interference (influences of platinum oxides such as 206PtO and 208PtO given to lead isotopes of 206Pb, 208Pb) is brought about in the measuring stage by the inductively coupled plasma mass spectrometry (ICP-MS), with the result that the accuracy of the analysis is lowered.

BRIEF SUMMARY OF THE INVENTION

According to the present invention, there is provided a method for the quantitative analysis of a metal element contained in a resin material, comprising:

decomposing the resin material within a container having at least the inner surface formed of a glassy carbon in the presence of an aqueous solution of an oxidizing acid;

heating the organic residue of the decomposed resin material so as to convert the residue into an ash; and quantitatively measuring the metal element contained in the organic residue converted into the ash.

BRIEF DESCRIPTION OF THE SEVERAL VIEWS OF THE DRAWING

The single FIGURE is a graph showing the result of the quantitative analysis for Example 4 and Comparative Example 5.

DETAILED DESCRIPTION OF THE INVENTION

The following describes the method for the quantitative analysis of a metal element contained in a resin material according to an embodiment of the present invention.

[First Step]

A resin material that is to be analyzed is decomposed within a container having at least the inner surface formed of a glassy carbon. The resin material is decomposed in the presence of an aqueous solution of an oxidizing acid.

The method for the quantitative analysis for this embodiment makes it possible to overcome various obstructions raised in the chemical pretreatment such as evaporation and adsorption. Thus, the method for the quantitative analysis of the embodiment can be applied to the resin material used in every manufacturing process which is not particularly limited.

The resin material analyzed in the embodiment, which is not particularly limited, includes, for example, plastic materials such as polyethylene (PE), polyvinyl chloride (PVA), and ABS, synthetic rubbers and paint components. It is possible for the resin material to be a single resin material or a composite material containing a resin material and another material. The composite material includes, for example, a resin composition having, for example, a filler mixed therein, a laminate body prepared by laminating a plurality of resin material layers, and a fiber-reinforced resin material prepared by mixing fibers in a resin material.

It is desirable for the resin material to be formed of a material constituting a part of an electronic appliance. The part of the electronic appliance includes, for example, a printing wiring board, a flexible printed board, and a package material.

The metal elements contained in the resin material and subjected to the quantitative analysis include, for example, Pb and Cd. It is possible for each of these metal elements to be contained in the resin material in the form of an ion, a molecule or any type of the chemical species. Also, it is possible for the metal elements to be present in the resin material in the form of any of a solid phase or a liquid phase.

The container having at least the inner surface formed of a glassy carbon includes, for example, (1) a container comprising a container body formed of a ceramic material such as boron carbide or tungsten carbide and a glassy carbon layer formed on the inner surface of the container body, and (2) a container formed of a glassy carbon. The glassy carbon used for forming the container has a glassy dense texture structure and is excellent in gas impermeability, the wear resistance, the corrosion resistance and the resistance to contamination.

Container 1 noted above can be manufactured by coating at least the inner surface of a container body formed of a ceramic material such as boron carbide or tungsten carbide with a resin composition containing a thermosetting resin such as polytetrafluoro ethylene (PTFE) or a denatured PTFE, followed by baking and carbonizing the resin composition under an inert gas atmosphere or under vacuum so as to form a glassy carbon layer on at least the inner surface of the container body. It is desirable for the glassy carbon layer to have a thickness of 10 to 100 $\mu$m.

Container 2 noted above can be manufactured by molding a resin composition containing a thermosetting resin such as polytetrafluoro ethylene (PTFE) or a denatured PTFE into the shape of a container, followed by baking and carbonizing the molding under an inert gas atmosphere or under vacuum so as to convert the resin composition into a glassy carbon.

It is desirable for the glassy carbon formed on at least the inner surface of the container to have a high smoothness, e.g., at most 10 $\mu$m of the surface roughness (center line average roughness: Ra). The high smoothness can be achieved by, for example, polishing the glassy carbon formed on at least the inner surface of the container. The center line average roughness (Ra) can be measured by using "Talysurf 5" (trade name of a surface roughness meter manufactured by Tailor Hobson Inc.). By setting the surface roughness of the glassy carbon at 10 $\mu$m or less, it is possible to suppress the deterioration of the surface state of the glassy carbon in the subsequent high temperature process for the ashing (carbonizing) treatment. As a result, it is possible to inhibit the influence given by the carbon reaction product to the analytical value. Particularly, it is desirable for the center line average roughness (Ra) of the glassy carbon to fall within a range of 0.1 to 1 $\mu$m.

The oxidizing acid includes, for example, sulfuric acid, hydrochloric acid, perchloric acid, nitric acid, hydrofluoric acid, phosphoric acid, and hydrogen peroxide. Particularly, it is desirable for the oxidizing acid to be formed of a mixed acid consisting of sulfuric acid and nitric acid.

It is desirable for the aqueous solution of the oxidizing acid to have a concentration of 10 to 50%, preferably 20 to 30%. If the concentration of the aqueous solution of the oxidizing acid is lower than 10%, the function of the aqueous solution as the oxidizing agent tends to be lowered markedly. On the other hand, if the concentration of the aqueous solution of the oxidizing acid exceeds 50%, a chemical reaction is rapidly brought about within the container between the oxidizing acid and the resin material, with the result that the metal element that is to be measured tends to be scattered.

When the resin material is decomposed within the container in the presence of the aqueous solution of the oxidizing acid, it is acceptable to dispose the container on, for example, a hot plate so as to heat the container at 100 to 200° C. According to the heat treatment with the temperature, the decomposition reaction can be finished within a practical time so as to develop the analytical efficiency.

It is desirable for the decomposition of the resin material to be finished at the time when the resin material is colored black. Where the container is heated at 100 to 200° C., it is desirable for the reaction time reaching the end point of the reaction to be 30 minutes to 2 hours. It is possible for the reaction of the resin material to be carried out under the atmospheric pressure or a reduced pressure.

[Second Step]

The residue of the resin material that was subjected to the decomposition treatment in the first step is heated to carbonize. Then, the carbonized residue is cooled to room temperature. The metal element contained in the carbonized residue is present in the container in the form of the oxide.

To be more specific, after the organic material of the resin material varies colored black in the first step, the heating temperature is elevated to 500° C. or lower, preferably to about 450° C., so as to decompose completely the organic material. Where, for example, an aqueous solution of sulfuric acid is used as the aqueous solution of the oxidizing acid, Pb or Cd is present in this stage in the form of the sulfate thereof, with the result that the metal element noted above is present in the oxidizing aqueous solution with a high stability even if the high temperature is maintained in the aqueous solution. Also, by elevating the heating temperature to 500° C. or lower, preferably to about 450° C., the organic material is converted into carbon dioxide so as to be separated from the aqueous solution, with the result that it is possible to remove the main component of the resin material.

It is desirable for the lower limit of the heating temperature i.e., the carbonizing temperature, which is not particularly limited in the present invention, to be set at 300° C., preferably at 400° C. If the carbonizing temperature is lower than 300° C., the carbonization does not proceed in the residue of the resin material. Even if the carbonization proceeds, a long time tends to be required for finishing the carbonization.

It is desirable for the processing time required for the carbonization, which differs depending on, for example, the amount of the resin material and the processing temperature, to fall within a range of 6 to 30 minutes.

[Third Step]

The metal element contained in the residue in the form of the oxide after the carbonizing process carried out in the second step is subjected to the quantitative analysis.

The method for the quantitative analysis of the metal element includes, for example, the wet chemical analytical method (weight method, titration method, absorptiometric analysis), the atomic absorption spectrometry (AAS), the ICP mass spectrometry (ICP-MS), the inductively coupled plasma-atomic emission spectrometry (ICP-AES), the electrically thermal atomic absorption spectrometry, and the ion chromatography. Among these methods, it is advisable to use the inductively coupled plasma mass spectrometry (ICP-MS apparatus) because the ICP-MS apparatus is advantageous in that (1) a large number of elements (about 64 elements) can be analyzed, (2) the analysis can be performed with a high sensitivity and, thus, the limit of detection is low (ppb to ppt), (3) the calibration curve has a wide straight region, (4) a large number of elements can be analyzed simultaneously, and (5) the qualitative and quantitative analysis can be performed promptly.

The inductively coupled plasma mass spectrometer, in which the plasma generated by a high frequency electromagnetic wave is used for exciting the atom, is featured in that a large number of elements can be measured simultaneously with a high sensitivity. Incidentally, the inductively coupled plasma mass spectrometer comprises a plasma torch, a mass spectrometer portion, and a detector. The sample is transferred by a carrier gas such as an Ar gas within the apparatus so as to be analyzed.

If a sample solution prepared by using a platinum crucible is used in the analysis performed by using the analytical apparatus noted above, the oxides of the platinum element, i.e., 206PtO and 208PtO eluted from the platinum crucible into the sample solution, perform an interference with the isotopes of lead, i.e., 206Pb and 208Pb, thereby inhibiting the detection of lead. However, the particular inconvenience can be avoided by using a container having at least the inner surface formed of a glassy carbon as described previously in conjunction with the first and second steps.

In the analysis performed by using the analyzing apparatus noted above, a solution prepared by dissolving in an acid the residue after the carbonizing process in the second step is used as the analytical sample. An inorganic acid of a high purity can be used for dissolving the carbonized residue. To be more specific, an inorganic acid such as nitric acid can be used for dissolving the carbonized residue.

According to the embodiment described above, it is possible to quantitatively analyze highly volatile metal elements contained in a resin material such as Pb and Cd as well as the metal elements that might have been introduced from the outside by contamination. The quantitative analysis can be performed at a high precision.

As described previously, it was customary in the past to use the wet acid decomposition method using an acid or a carbonizing method using a platinum crucible for the quantitative analysis of the harmful elements contained in the part of the electronic appliances. In these analytical methods, however, it was difficult to analyze quantitatively the metal elements noted above with a high accuracy because the optimum method for the quantitative analysis of highly volatile metal elements such as Pb and Cd and the metal elements that might have been introduced from the outside by contamination has not yet been established. As described previously, platinum forms a solid solution with the metal element such as Pb. Therefore, in the case of using a platinum crucible, Pb is adsorbed on the wall of the platinum crucible. Also, Pb is eluted as an impurity from the platinum crucible, or elution of the platinum itself is generated.

According to the embodiment, the resin material to be analyzed is housed in a container having a glassy carbon layer formed on at least the inner surface. The glassy carbon exhibits the merits of both the quartz glass and the fluoroplastics, has a glassy dense texture structure and is excellent in gas impermeability, the wear resistance, the corrosion resistance and the resistance to contamination. The resin material is decomposed within the container having a glassy carbon layer formed on at least the inner surface, and the decomposition is carried out in the presence of an aqueous solution of an oxidizing acid such as sulfuric acid. As a result, volatile metal elements contained in the resin material such as Pb and Cd and the metal elements that might have been introduced from the outside by contamination are allowed to be present under a stable state within the container in the form of the sulfates, thereby suppressing the dissipation of the metal elements noted above. Also, since the glassy carbon layer formed on the inner surface of the container exhibits excellent characteristics as pointed out above, the metal elements are prevented from performing the reaction with the glassy carbon formed on the inner surface of the container when the organic material constituting the main component of the resin material is separated and removed in the carbonizing step, with the result that the metal element noted above is allowed to be present in the residue. Even if the polyvinyl chloride resin containing a large amount of chlorine (Cl) is used as a resin material to be analyzed, the metal element is prevented from performing the reaction with chlorine and, thus, prevented from being dissipated in the form of the chloride of the metal element. It follows that the metal element is allowed to be present in the residue. Further, in the decomposition process and the carbonization process, the glassy carbon layer formed on the inner surface of the container does not react with the resin material, though the reaction with the resin material is brought about in the case of using the conventional platinum crucible. Also, since the amount of the impurity metal eluting from the glassy carbon layer is very small, it is possible to suppress markedly the obstacle to the quantitative analysis of the metal elements to be analyzed such as Pb or Cd. To be more specific, the impurity metal contained in the solution is at least one metal selected from the group consisting of platinum, boron and tungsten, and the amount of the impurity metal can be decreased to 1 ppm or less.

As described above, the solution to be used is prepared from the residue free from the contamination from the material other than the resin material, e.g., the contamination from the container, and free from the influence given by the obstacle to the analysis is subjected to the quantitative analysis in the present invention by the ICP-MS, the inductively coupled plasma-atomic emission spectrometry (IPC-AES) or the atomic absorption spectrometry (AAS). The particular method of the present invention makes it possible to analyze quantitatively the volatile metal elements contained in the resin material such as Pb and Cd and traces of metal elements harmful to the environment, which might have been introduced from the outside by contamination, at a high accuracy in a short time, though a long troublesome measurement was required in the past for the quantitative analysis of the metal elements noted above. Under the circumstances, it is possible to secure the safety of the environment within the manufacturing facilities of the part of the electronic appliances and to improve the reliability of the product in the industry for supervising the materials of, for example, the part of the electronic appliances.

It should be noted in particular that the reactivity of the container with the oxidizing acid such as sulfuric acid is markedly suppressed in the container having at least the inner surface formed of a glassy carbon, the glassy carbon having the surface roughness (center line average roughness [Ra]) not larger than 10 μm. It follows that the container is capable of retaining a highly stable shape even under high temperatures. As a result, it is possible to permit the highly volatile metal elements contained in the resin material such as Pb and Cd and the metal elements that might have been introduced from the outside by contamination to be present in a stable form in the decomposing process noted above. Also, when the organic material constituting the main component of the resin material is separated and removed in the subsequent carbonizing step, it is possible to permit the metal elements noted above not to be dissipated and, thus, to be present as a residue. In addition, it is possible to further decrease the amount of the impurities eluting from the glassy carbon layer so as to suppress markedly the obstacle to the quantitative analysis of the metal elements to be analyzed such as Pb and Cd. It follows that it is possible to carry out the quantitative analysis of the volatile metal elements contained in the resin material such as Pb and Cd and the metal elements that might have been introduced from the outside by contamination with a further improved accuracy by preparing the sample solution from the residue noted above and by carrying out the quantitative analysis by using the inductively coupled plasma-atomic emission spectrometry (IPC-AES) referred to above.

The present invention will now be described more in detail with reference to Examples of the present invention.

EXAMPLE 1

Prepared as a sample was a European polyethylene standard substance (BCR-680, BCR 681) the measured value of which is guaranteed.

0.2 g of the sample was housed in a cylindrical container having the bottom and made of a glassy carbon having 1 μm of the center line average roughness Ra on the inner surface. The center line average roughness Ra was measured by using "Talysurf 5" (trade name of a surface roughness meter manufactured by Taylor Hobson Inc. Then, 5 mL of an aqueous solution of nitric acid having a concentration of 30% by weight and 5 mL of an aqueous solution of sulfuric acid having a concentration of 30% by weight were put in the container, followed by putting the container on a hot plate and heating the container at 150° C. so as to decompose the sample (standard substance made of polyethylene). Further, the container made of the glassy carbon was set within a muffle furnace, and the sample was carbonized at 450° C. so as to remove sulfuric acid, nitric acid and the organic material. After the container was cooled to room temperature, 5 mL of an aqueous solution of nitric acid having a concentration of 30% by weight was put in the container so as to dissolve the residue, thereby preparing a sample solution. The sample solution thus prepared was analyzed by using an inductively coupled plasma mass spectrometry SPQ 9000 manufactured by Seiko Denshi Kogyo K.K. In this analysis, the high frequency output of the mass spectrometry was set at 1.1 kW. Incidentally, a coaxial nebulizers made of quartz was used for introducing the sample solution into the inductively coupled plasma mass spectrometry. Concerning the mass numbers to be measured, the mass number of Cr was 52, the mass number of Cd was 111, and the mass number of Pb was 208. Table 1 shows the result of the quantitative analysis.

COMPARATIVE EXAMPLE 1

A sample solution was prepared by using a sample similar to that used in Example 1. Then, 5 mL of sulfuric acid and 10 mL of nitric acid were added to the sample in accordance with the standards specified in BSEN-1122 so as to control finally the sulfuric acid concentration at 5% by weight. The sample solution thus prepared was put in a low resolution inductively coupled plasma mass spectrometry SPQ 9000 manufactured by Seiko Denshi Kogyo K.K. In this analysis, the high frequency output of the mass spectrometry was set at 1.1 kW. Incidentally, a coaxial nebulizers made of quartz was used for introducing the sample solution into the inductively coupled plasma mass spectrometry. Concerning the mass numbers to be measured, the mass number of Cr was 52, the mass number of Cd was 111, and the mass number of Pb was 208. Table 1 shows the result of the quantitative analysis.

COMPARATIVE EXAMPLE 2

A sample similar to that used in Example 1 was subjected to a carbonizing treatment within a platinum crucible set at 550° C. in accordance with the standards specified in ISO 6101. The solution resulting from the decomposition of the sample was put in a low resolution inductively coupled plasma mass spectrometry SPQ 9000 manufactured by Seiko Denshi Kogyo K.K. In this analysis, the high frequency output of the mass spectrometry was set at 1.1 kW. Incidentally, a coaxial nebulizers made of quartz was used for introducing the sample solution into the inductively coupled plasma mass spectrometry. Concerning the mass numbers to be measured, the mass number of Cr was 52, the mass number of Cd was 111, and the mass number of Pb was 208. Table 1 shows the result of the quantitative analysis.

Table 1 also shows the guaranteed values of the metal elements that were measured.

TABLE 1

| Resin material (sample) | Measured value (μg/g) | | | Guaranteed value (μg/g) | | |
|---|---|---|---|---|---|---|
| | Pb | Cd | Cr | Pd | Cd | Cr |
| Example 1 BCR-680 | 105.5 | 141.2 | 112.5 | 107.6 ± 2.8 | 140.8 ± 2.5 | 114.6 ± 2.6 |
| BCR-681 | 13.4 | 21.2 | 17.5 | 13.8 ± 0.7 | 21.7 ± 0.7 | 17.7 ± 0.6 |
| Comparative BCR-680 | 43.3 | 142 | 113.7 | 107.6 ± 2.8 | 140.8 ± 2.5 | 114.6 ± 2.6 |
| Example 1 BCR-681 | 9.5 | 21.5 | 17.3 | 13.8 ± 0.7 | 21.7 ± 0.7 | 17.7 ± 0.6 |
| Comparative BCR-680 | 350 | 95 | 113.8 | 107.6 ± 2.8 | 140.8 ± 2.5 | 114.6 ± 2.6 |
| Example 2 BCR-681 | 100 | 13 | 18.2 | 13.8 ± 0.7 | 21.7 ± 0.7 | 17.7 ± 0.6 |

As apparent from Table 1, the measured value well conformed with the guaranteed value in spite of the use of sulfuric acid in Example 1 in which was used a cylindrical container having the bottom and made of a glassy carbon. That is, the quantitative analysis of Pb and Cd can be carried out with a high accuracy in the method of Example 1.

On the other hand, the measured value of Pb for Comparative Example 1, in which the quantitative analysis was performed in accordance with BS-1122, was found to be markedly smaller than the guaranteed value, indicating that it was impossible to obtain an accurate value. It should be noted in this connection that sulfuric acid having a high concentration was added in Comparative Example 1 so as to cause Pb to have precipitated in the form of lead sulfate, with the result that the Pb concentration was lowered.

Also, in Comparative Example 2, the measured value of Cd, which was measured in accordance with ISO 6106, was markedly smaller than the guaranteed value. In addition, the measured value of Pb was markedly increased, compared with the guaranteed value, resulting in failure to obtain an accurate value. It should be noted in this connection that, since the process temperature was high, the measured value of Cd was small and the measured value of Pb was markedly increased because of the influence given by PtO.

EXAMPLE 2

Prepared were three kinds of cylindrical containers each having the bottom and made of a glassy carbon. These containers differed from each other in the center line average roughness (Ra) of the glassy carbon on the inner surface. Specifically, the center line average roughness (Ra) of the glassy carbon on the inner surface, which was measured by a surface roughness meter "Talysurf 5" manufactured by Taylor Hobson Inc. was 1,000 μm, 100 μm or 10 μm. The container had an inner diameter of 70 mm and a height of 80 mm. Then, 10 mL of an aqueous solution of sulfuric acid having a concentration of 30% by weight was housed in each of these containers. Further, each of these containers was set in a muffle furnace and heated stepwise to 400° C., 450° C., 500° C., 550° C. and then to 600° C. so as to measure the center line average surface roughness Ra on the inner surface of the container at each of the heated temperatures by using the surface roughness meter noted above. Table 2 shows the result.

TABLE 2

| Center line average roughness before | Center line average roughness after heating (μm) | | | | |
|---|---|---|---|---|---|
| heating (μm) | 400° C. | 450° C. | 500° C. | 550° C. | 600° C. |
| 1000 | 1100 | 1300 | 2000 | 2200 | Impossible to measure |
| 100 | 120 | 140 | 200 | 280 | 1200 |
| 10 | 10 | 10 | 10 | 20 | 30 |

As apparent from Table 2, the container made of a glassy carbon having not larger than 10 μm of the center line average roughness Ra on the inner surface was found to be low in deterioration even under a high temperature region, supporting that the particular container exhibited an excellent stability.

EXAMPLE 3 AND COMPARATIVE EXAMPLE 3

Sample solutions were prepared by the methods similar to those for Example 1 and Comparative Example 2 by using the standard sample (BCR-680) equal to that used in Example 1, and the quantitative analysis was applied to isotope elements of lead. FIG. 1 shows the result.

As apparent from FIG. 1, in Comparative Example 3 using a platinum crucible, the detection of 206Pb and 208Pd was much obstructed by the obstruction by platinum, compared with Example 3 using a container made of a glassy carbon.

Needless to say, the present invention is not limited to the embodiment described above. The embodiment is no more than an example. The method having the construction substantially equal to the technical idea recited in the accompanying claims and producing the similar function and effect is included in the technical scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for the quantitative analysis of a metal element contained in a resin material, comprising:
   decomposing a resin material within an aqueous solution of an oxidizing acid to produce an organic residue in a container, said container comprising a container body made of a ceramic material and a glassy carbon layer formed on the inner surface of the container body, wherein said container accommodates said aqueous solution of an oxidizing acid;
   heating the organic residue of the resin material so as to convert the residue into an ash; and
   quantitatively measuring the metal element contained in the ash.

2. The method according to claim 1, wherein the ceramic material is selected from the group consisting of boron carbide and tungsten carbide.

3. The method according to claim 1, wherein the oxidizing acid is at least one selected from the group consisting of sulfuric acid, hydrochloric acid, perchloric acid, nitric acid, hydrofluoric acid, phosphoric acid and hydrogen peroxide.

4. The method according to claim 1, wherein the oxidizing acid is a mixed acid consisting of sulfuric acid and nitric acid.

5. The method according to claim 1, wherein the aqueous solution of the oxidizing acid has a concentration of 10 to 50% by weight.

6. The method according to claim 1, wherein the decomposition of the resin material is performed by heating the container to 100 to 200° C.

7. The method according to claim 1, wherein the heating of the organic residue is carried out at 300 to 500° C.

8. The method according to claim 1, wherein the metal element is quantitatively analyzed by dissolving the residue with an acid, wherein the amount of an impurity metal in the solution is not larger than 1 ppm.

9. The method according to claim 8, wherein the impurity metal is at least one metal selected from the group consisting of platinum, boron and tungsten.

10. The method according to claim 1, wherein the quantitative analysis of the metal element is carried out by using an inductively coupled mass spectrometry.

11. The method according to claim 1, wherein the resin material is at least one selected from the group consisting of polyethylene, polyvinyl chloride, and acrylonitrile butadiene styrene.

12. The method according to claim 1, wherein the resin material is a part of an electronic appliance.

13. The method according to claim 12, wherein the part of the electronic appliance is selected from the group consisting of a printing wiring board, a flexible printed board and a package material.

14. The method according to claim 1, wherein the metal element is Pd or Cd.

15. A method for the quantitative analysis of a metal element contained in a resin material, comprising
   decomposing the resin material within a container having at least the inner surface formed of a glassy carbon layer in the presence of an aqueous solution of an oxidizing acid;

heating the organic residue of the decomposed resin material so as to convert the residue into an ash; and quantitatively measuring the metal element contained in the organic residue converted into the ash wherein the glassy carbon layer formed on the inner surface of the container has a surface roughness not higher than 10 μm.

16. A method for the quantitative analysis of a metal element contained in a resin material, comprising decomposing the resin material within a container having at least the inner surface formed of a glassy carbon layer in the presence of an aqueous solution of an oxidizing acid;

heating the organic residue of the decomposed resin material so as to convert the residue into an ash; and quantitatively measuring the metal element contained in the organic residue converted into the ash wherein the glassy carbon layer formed on the inner surface of the container has a surface roughness of 0.1 to 1 μm.

* * * * *

UNITED STATES PATENT AND TRADEMARK OFFICE
CERTIFICATE OF CORRECTION

PATENT NO. : 7,727,767 B2 Page 1 of 1
APPLICATION NO. : 11/517407
DATED : June 1, 2010
INVENTOR(S) : Takenaka et al.

It is certified that error appears in the above-identified patent and that said Letters Patent is hereby corrected as shown below:

On the title page, Item (73), the Assignee should read:

-- (73) Assignee: Kabushiki Kaisha Toshiba, Tokyo (JP) --

Signed and Sealed this

Tenth Day of August, 2010

David J. Kappos
*Director of the United States Patent and Trademark Office*